CHRYSANTHEMUM PLANT
Filed Sept. 11, 1973
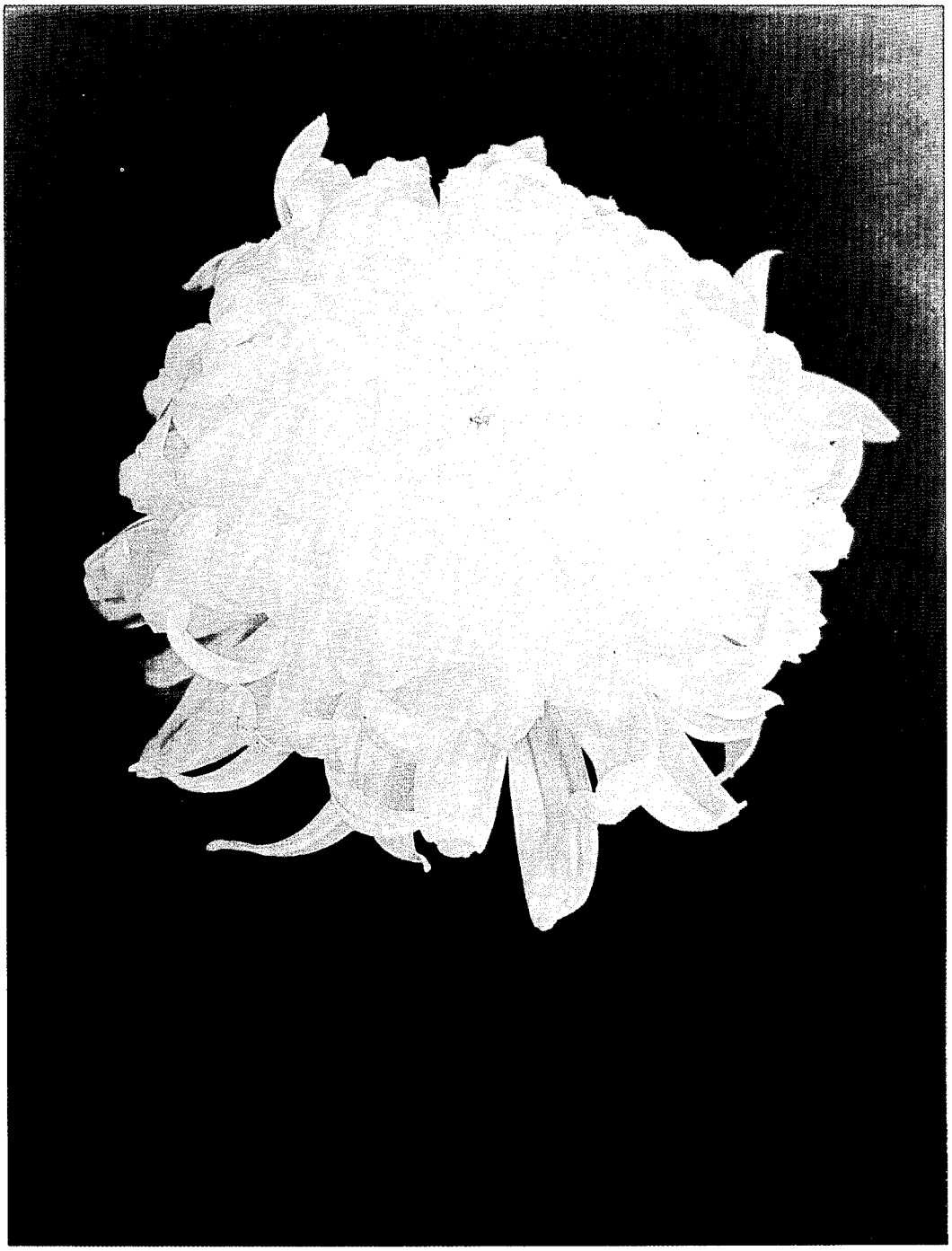

United States Patent Office

Plant Pat. 3,659

Patented Nov. 26, 1974

3,659
CHRYSANTHEMUM PLANT

Walter H. Jessel, Jr., Doylestown, and William E. Duffett, Akron, Ohio, assignors to Yoder Brothers, Inc., Barberton, Ohio

Filed Sept. 11, 1973, Ser. No. 396,129
Int. Cl. A01h *5/00*

U.S. Cl. Plt.—77 1 Claim

The present invention comprises a new and distinct cultivar of chrysanthemum plant known by the varietal name Arcade which is a seedling of #66088002× #65138002. Both parents are unpatented and identified for breeding purposes by the above breeding numbers.

The new cultivar is similar in certain respects to Jumbo Albatross, described and illustrated in U.S. Plant Patent 3,249, having the same characteristics as Jumbo Albatross of:

1. Excellent shipping and handling qualities.
2. A requirement for relatively high light intensities in combination with moderate night temperatures to develop optimum flower size and form.

The new cultivar is distinguished from Jumbo Albatross by the following characteristics when grown under comparable conditions:

1. A year round period of value in Coastal California.
2. A whiter flower color.
3. A more incurved flower form.
4. Better form retention, having approximately 2–4 days greater bench life.
5. Improved stem strength and stem caliper.
6. 4–7 days earlier response.
7. Approximately 8 inches more vigor.
8. Approximately 1 inch larger flower size.
9. Less tolerant to marginal temperatures (56° F.) for uniform bud initiation.
10. A greater sensitivity to mildew.

11. Requires more attention to prompt lateral bud removal in order to obtain maximum size.

The new cultivar was selected from the progeny of the designated cross, and when asexually reproduced by cuttings at Barberton, Ohio, has been found to retain its distinctive characteristics through successive propagation.

The new cultivar, when grown in the vicinity of Salinas, California, has a late 7 week response period March through June and October through November, and an early 8 week response December through February and July through September. The following detailed description is based on observations made of the new cultivar in a greenhouse in Salinas, California. The response time, blooming period, color, and total vigor may vary significantly with varying environmental conditions such as temperature, daylength, and light intensity. Suggested flowering in the northern United States is from April 15 through May 30 and October 1 through November 15; southeastern United States, March 1 through April 30 and October 15 through November 15; southwestern United States, March 1 through April 30 and October 15 through November 15; coastal California, year round, and southern Floride under outdoor conditions, December 15 through March 15.

The accompanying photographic drawing comprises a specimen photograph of the new cultivar and shows the unique characteristics thereof. The color is as nearly true as possible with color illustrations of this type. Color references in the following description are made to the Munsell Book of Color, 1963 Edition, with the exception of Arcade's top side leaf color where reference is made to Munsell Limit Color Cascade, 1972 Edition, and comparisons are made with the cultivar Jumbo Albatross. Where only a single value or description appears for the new cultivar, the same value or description applies as well to Jumbo Albatross.

Botanical classification: *Chrysanthemu n morifolium*

| | Arcade | Jumbo Albatross |
|---|---|---|
| Bloom: | | |
| Size | 6″ | 5½″. |
| Fully expanded | 6½″ | 6″. |
| Borne | Singly on disbudded plants. | |
| Stems | Strong and sturdy | Strong. |
| Form | Tight incurve | Incurve. |
| Permanence | 12–14 days | 10 days. |
| Color: | | |
| Center of flower | Pale ivory, 5Y9/1 | Pale yellow, 7.5Y9/4. |
| Base of petals | do | Ivory white, 5Y9/1. |
| Inside of petals | White, N9.5/ | Do. |
| Reverse of petals | White, N9/ | Do. |
| Tonality from a distance | White | Ivory white. |
| Discoloration | White, N9.5 | Ivory white, 5Y9/1. |
| Petals: | | |
| Texture | Smooth with occasional seta on reverse | Smooth. |
| Appearance and form | Open at base with wide rounded keel, tapering to a blunt hooded tip. | Tubular at base, deep rounded keel, tapering to a hooded blunt tip with characteristics finger-like appendages on side of keel. |
| Arrangement | Composite, whorled on a single receptacle | |
| Persistence | Resist shatter | |
| Fragrance | Typical chrysanthemum | |
| Reproductive organs: | | |
| Stamen, anthers | 5–15 | 0–5. |
| Pollen | None to very scant | |
| Arrangement | Clustered in center of flower, if present | |
| Styles | Present both ray and disc florets | |
| Length | Short | |
| Ovaries | At the base of petal attached to receptacle | |
| Plant: | | |
| Form | Herbaceous | |
| Growth | Upright | |
| Height | 44″–46″ given 3–6 long day weeks, and 10–14 weeks total crop time year round, as defined in the timetables of Yoder Brothers, Inc., Barberton, Ohio. | 36″–38″ given 3–4 long day weeks, and 11–12 week total crop time (April through November only), as defined in the timetables of Yoder Brothers, Inc., Barberton, Ohio. |
| Spread | None grown single stem to slight grown pinched | |
| Foliage: | | |
| Top side | Very dark green 8.9GY2.3/4.7 | Dark green 2.5GY2/4. |
| Size | Width to length ratio 25:14 with width to 3½″ and length to 6¼″. | Width to length ratio 13:23 with length to 5¾″ and width to 3¼″. |
| Quantity | Numerous | |
| Shape | Spatulate lobed | |
| Texture | Moderately coarse | Smooth. |
| Ribs and veins | Prominent | |
| Edge | Deeply indented | Moderately indented. |
| Serration | Coarse | Very slight. |
| Under side | Greyed green, 2.5GY3/4 | Greyed green, 2.5GY4/4. |
| Stipules | Prominent | Small. |

We claim:

1. A new and distinct cultivar of chrysanthemum characterized particularly as to its uniqueness when compared to the cultivar Jumbo Albatross by its year round period of value in Coastal California; whiter flower color; more incurved flower form; better form retention, having approximately 2–4 days greater bench life; improved stem strength and stem caliper; 4–7 days earlier response; approximately 8 inches more vigor; approximately 1 inch larger flower size; less tolerant to marginal temperatures (56° F.) for uniform bud initiation; greater sensitivity to mildew, and by its requiring more attention to prompt lateral bud removal in order to obtain maximum flower size.

No references cited.

ROBERT E. BAGWILL, Primary Examiner